United States Patent [19]
Sloane, Jr. et al.

[11] Patent Number: 5,425,903
[45] Date of Patent: Jun. 20, 1995

[54] LASER BEVELING PROCESS FOR CATHETERS

[75] Inventors: Thomas E. Sloane, Jr., West Redding; Zinovy Altman, Bristol, both of Conn.; Anthony Y. Van Heugten, Longboat Key, Fla.

[73] Assignee: Critikon, Inc., Tampa, Fla.

[21] Appl. No.: 120,103

[22] Filed: Sep. 10, 1993

[51] Int. Cl.⁶ .............................................. B23K 26/00
[52] U.S. Cl. ..................... 264/22; 219/121.69; 264/25; 264/162; 604/264
[58] Field of Search ............... 264/22, 159, 162, 149, 264/25, 150; 156/272.8; 219/121.67, 121.69; 604/264, 280

[56] References Cited

U.S. PATENT DOCUMENTS

| | | | |
|---|---|---|---|
| 3,719,737 | 3/1973 | Vaillancourt et al. | 264/162 |
| 3,808,394 | 4/1974 | Mominee et al. | 264/25 |
| 4,551,292 | 11/1985 | Fletcher et al | 264/162 |
| 4,661,300 | 4/1987 | Daugherty | 264/163 |
| 4,963,306 | 10/1990 | Weldon | 264/149 |
| 5,102,324 | 4/1992 | Bullard et al. | 425/150 |
| 5,151,231 | 9/1992 | Lambert et al. | 264/162 |
| 5,209,882 | 5/1993 | Hattori et al. | 264/40.2 |
| 5,215,614 | 6/1993 | Wijkamp et al. | 264/162 |
| 5,240,537 | 8/1993 | Bodicky | 264/162 |
| 5,266,359 | 11/1993 | Spielvogel | 427/2 |

FOREIGN PATENT DOCUMENTS 4-236241  8/1992  Japan ..................... 264/22

*Primary Examiner*—Jeffery R. Thurlow
*Attorney, Agent, or Firm*—Joseph F. Shirtz

[57] ABSTRACT

A process and product and apparatus are disclosed wherein a laser is used to form a conical tapered tip on a catheter product. The catheter is placed on an insertion needle prior to the formation process, thus eliminating the problems associated with wearing out forming tooling. The process and product further call for the use of the laser to create a surface effect on the cannula to indicate the terminus of the catheter.

16 Claims, 8 Drawing Sheets

LASER BEVELING PROCESS FOR CATHETERS

BACKGROUND OF THE INVENTION

The present invention relates to a method and apparatus for forming catheter products and particularly to a method and apparatus for beveling the tip of intravenous catheters.

Intravenous catheters come substantially in two types of products. The first type is a through-the-needle catheter product wherein the catheter that is to be disposed within the vein is inserted through a sharpened cannula. The cannula is used to pierce the skin and insert the catheter and later is removed. However, this type of catheter has not met with much commercial success do to inherent flaws in the through-the-needle type delivery system. For example, the needle must be larger in diameter than the catheter being inserted. Therefore, the needle creates a larger opening on insertion than the catheter requires and creates a greater chance of leakage. Furthermore, it is difficult to remove and dispose of the needle or cannula once the catheter has been inserted.

The second and more common type of intravenous catheters is the over-the-needle catheter. In this type of product a needle or cannula has disposed thereover a catheter. The catheter is disposed such that the sharpened tip of the needle is extending from the catheter product and is used to pierce the patient's skin and insert the catheter. Once the skin and vein have been pierced, the catheter is threaded off of the needle and the needle is removed from the catheter product.

In order to ease the insertion of the over-the-needle type catheter products, it has long been known to bevel the tip of the catheter to provide a smooth transition between the surface or outer diameter of the needle or cannula and the surface or outer diameter of the catheter itself during the insertion process. There have been many methods developed for beveling the tips of catheters. For example, U.S. Pat. No. 4,661,300 to Daugherty entitled "Method and Apparatus for Flashless Tipping of an I.V. Catheter" discloses a process which was used in the early 1980's to mold a beveled tip on a catheter while simultaneously trimming the flash in order to provide a clean edge to the tip. This process, however, requires a high cost in retooling because of the wear interface between the two tool members and the cleaning necessary to unclog the mold from the trimmed flash.

Catheters have also been provided with what is actually a duel bevel. The bevel begins gently at approximately 3° and then is sharper right at the tip, for example 27°. The sharper bevel is provided to ease the transition to the initial OD of the catheter, while the softer bevel eases the opening to the final OD of the catheter.

SUMMARY OF THE INVENTION

Therefore, in order to eliminate the molding process of the prior art, the present invention provides for laser cutting or ablating of the polymer material, which forms the tubular sheath of the catheter. A catheter is normally formed of a hub of material for receiving a fitting at a proximal end of the catheter and a distal portion of tubular material. This tubular material may be preformed with a slight bevel on the outer surface with a final sharper bevel provided by the laser cutting process.

The process for beveling the tip comprises providing a source of coherent light such as laser light from an excimer laser, which has sufficient power to ablate, cut, melt or otherwise form the catheter material. The catheter is positioned in a path where it will intercept the coherent light and is rotated while positioned in that path. By positioning the catheter with the light path at an angle to the catheter material, the rotation will form a frustoconical surface of predetermined angularity.

Preferably, the current process is carried out with the catheter already in place on an insertion cannula or needle. Thus, the process may be controlled such that the bevel is formed at the very heal or bottom of the sharpened point of the needle so that a natural transition occurs between the sharpened point of the needle and the beginning of the catheter material.

BRIEF DESCRIPTION OF THE DRAWINGS

The invention will now be described with reference to the accompanying drawings wherein.

DESCRIPTION OF THE PREFERRED EMBODIMENT

Catheters are generally made of polymer materials and the substantial majority of intravenous catheters are either made of a polytetrafluoroethelyene (PTFE) material, such as Teflon TM as sold by E. I. du Pont de Nemours and Company, 1007 Market Street, Wilmington, DE 19898 and clear polyurethane materials. Certain polymers may be used to produce an optically clear radio opaque catheter, which permits visual inspection of the internal volume, while it may be located through the use of standard x-ray inspections.

Figure 1:
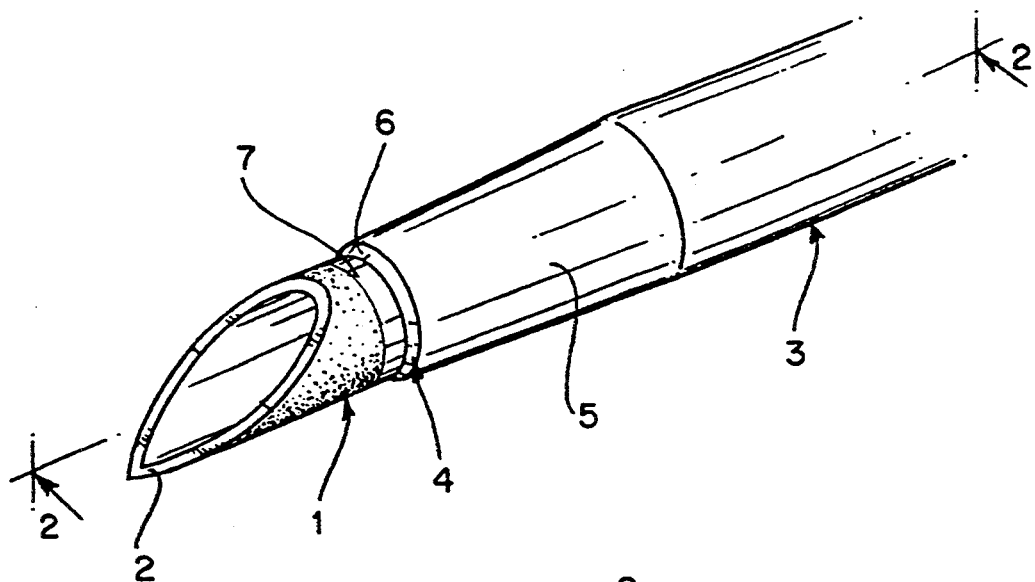
FIG. 1 is a perspective view of a catheter tip, including needle, made according to the present invention.
Figure 2:
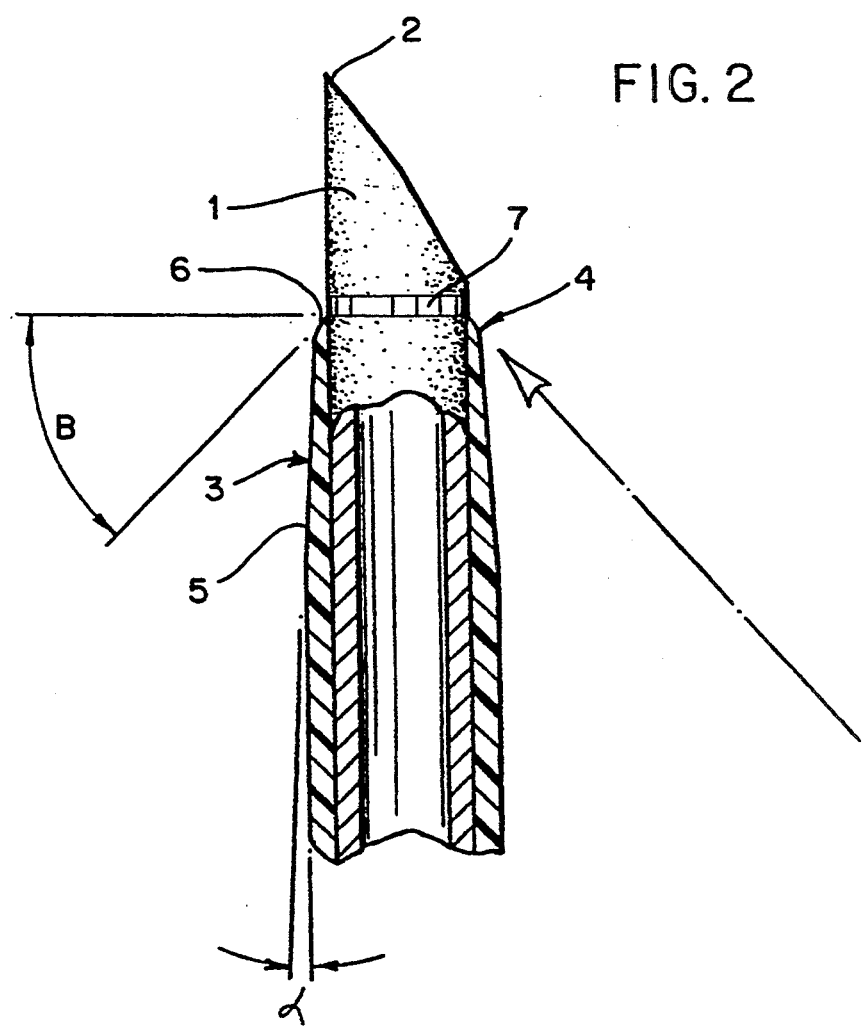
FIG. 2 is a partial cross-sectional view of a catheter of the invention.

The catheter includes a cannula 1, having a sharpened point 2, which is used to pierce the site of insertion of the catheter. The catheter 3 is disposed over the cannula 1 and has a tip 4, which provides the initial transition point between the cannula surface and the outer surface of the catheter. The catheter tip 4 is provided with a taper 5 and a bevel 6. The cannula is also provided in the present invention with a zone 7, which provides visual indication of the tip of the catheter. Referring to FIG. 2 it is seen that during the process of forming the catheter, the taper angle Alpha ($\alpha$), preferably approximately 3° but which may range from 1°-10° is formed on the tip of the catheter. A second angle, Beta ($\beta$), is formed at the end of the catheter tip in order to provide the transition between the surface of the cannula and the surface of the taper.

As will be described below, the angle alpha is initially formed on the catheter outer surface and the angle beta is formed by use of a laser cutting or ablation process which simultaneously removes the material from the catheter tip forming the bevel and which makes the indication zone 7 on the cannula.

Figure 3:
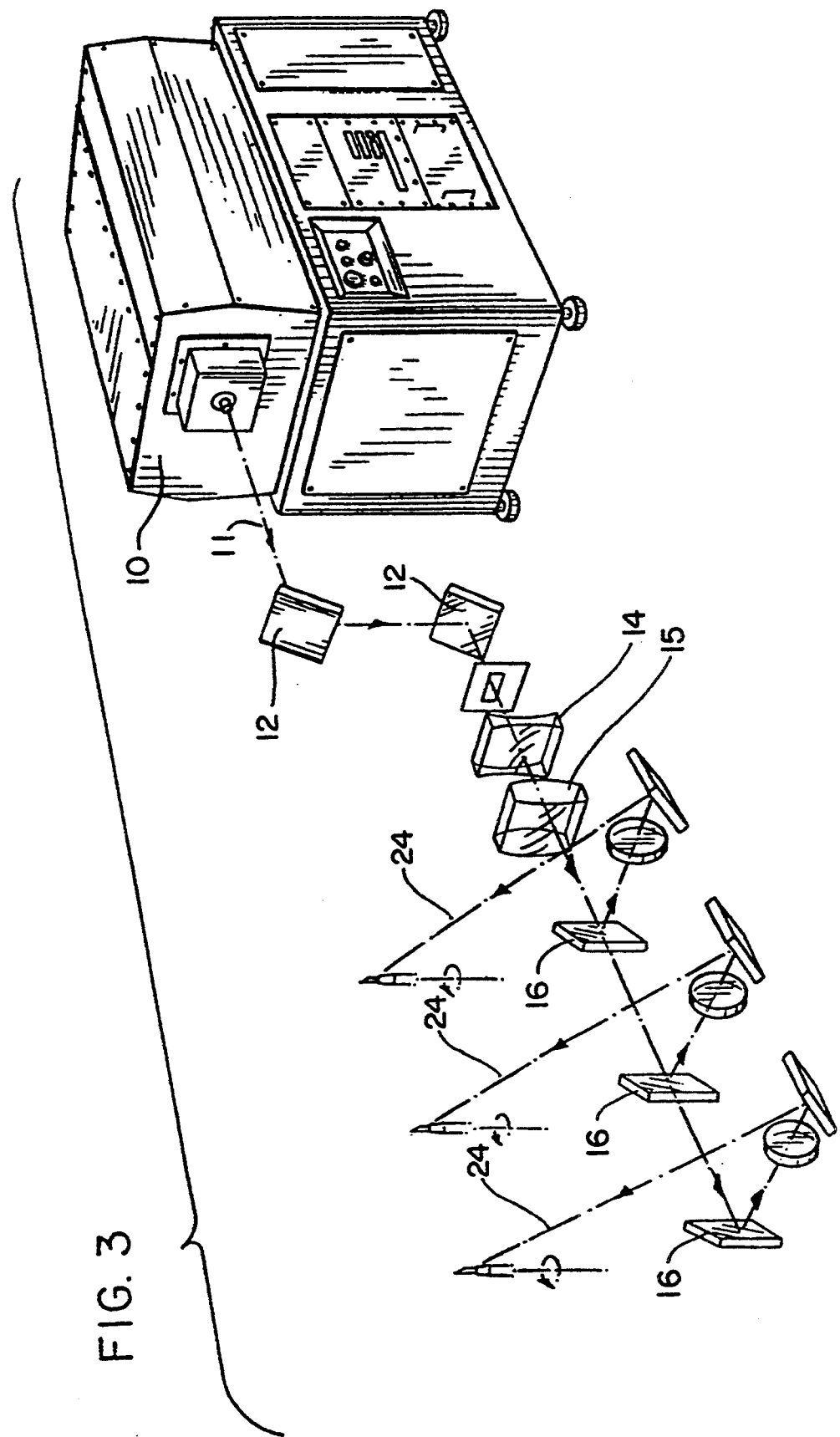
FIG. 3 is a schematic perspective view of a laser apparatus of the present invention.

Referring to FIG. 3, the source of this laser is indicated. As laser 10 is provided, which is particularly an excimer laser. For example, the excimer EX-748 laser as provided by Lumonics Inc. of Kanata, Ontario, Canada. The laser beam 11 is manipulated by mirrors 12 into a position running adjacent to the manufacturing apparatus. A masking slide 13 reduces the amount of energy provided ultimately to the apparatus by masking a portion of the beam prior to its focusing. The masking slide also acts as a preliminary beam shaping device to shape the beam prior to entering lens 14. Lenses 14 and 15 focus the beam and form a thin rectangular shape to the beam. Beam splitters 16 are provided, which permit passage of a certain percentage of the power while reflecting an initial percentage, such that three beams are provided, each having approximately ⅓ of the power delivered through the lenses 14 and 15.

By acting on the power and shape of the beam the mask 13 and lenses 14 and 15 can be used to shape the distal end of the catheter. The preferred embodiment of the mask is always 15 mm wide, that is, 15 mm in width across the beam. However, the height of the slit may be varied. The slit is rectangular and a preferred slit height is 0.8 mm. This provides an opening which is 0.8 mm by 15 mm to initially shape the beam. This preliminary shaped beam will provide a substantially flat conical surface to the catheter tip 4. An alternative embodiment creates a novel tip having a concave shape. This shape presents a softer profile to the entry point at the beginning of insertion and gradually increases as the catheter is inserted. That is the angle of attack of the surface is very close to the outer circumference of the needle at the very end of the catheter but the further away from the tip the greater the diameter gets in a slightly curved fashion. To provide such a shape a mask having a slit which is 3 mm high by 15 mm wide readily creates a concave structure to the tip.

Successful operations of catheter tipping have been run using polyurethane material and a laser pulse repetition rate of 180–190 pulses per second, with burst sizes ranging from 340–360 pulses. The total energy applied has ranged from 300 to 325 millijoules. Although these ranges were used experimentally, it is believed that much wider ranges will be operable without being beyond the scope of this invention. Furthermore, the selection of a three-beam split from a single beam is merely arbitrary in nature. A very small percentage of the total beam power is being used in the three-beam situation and therefore additional beam splits could be used if desired from an individual laser set up.

Figure 4:
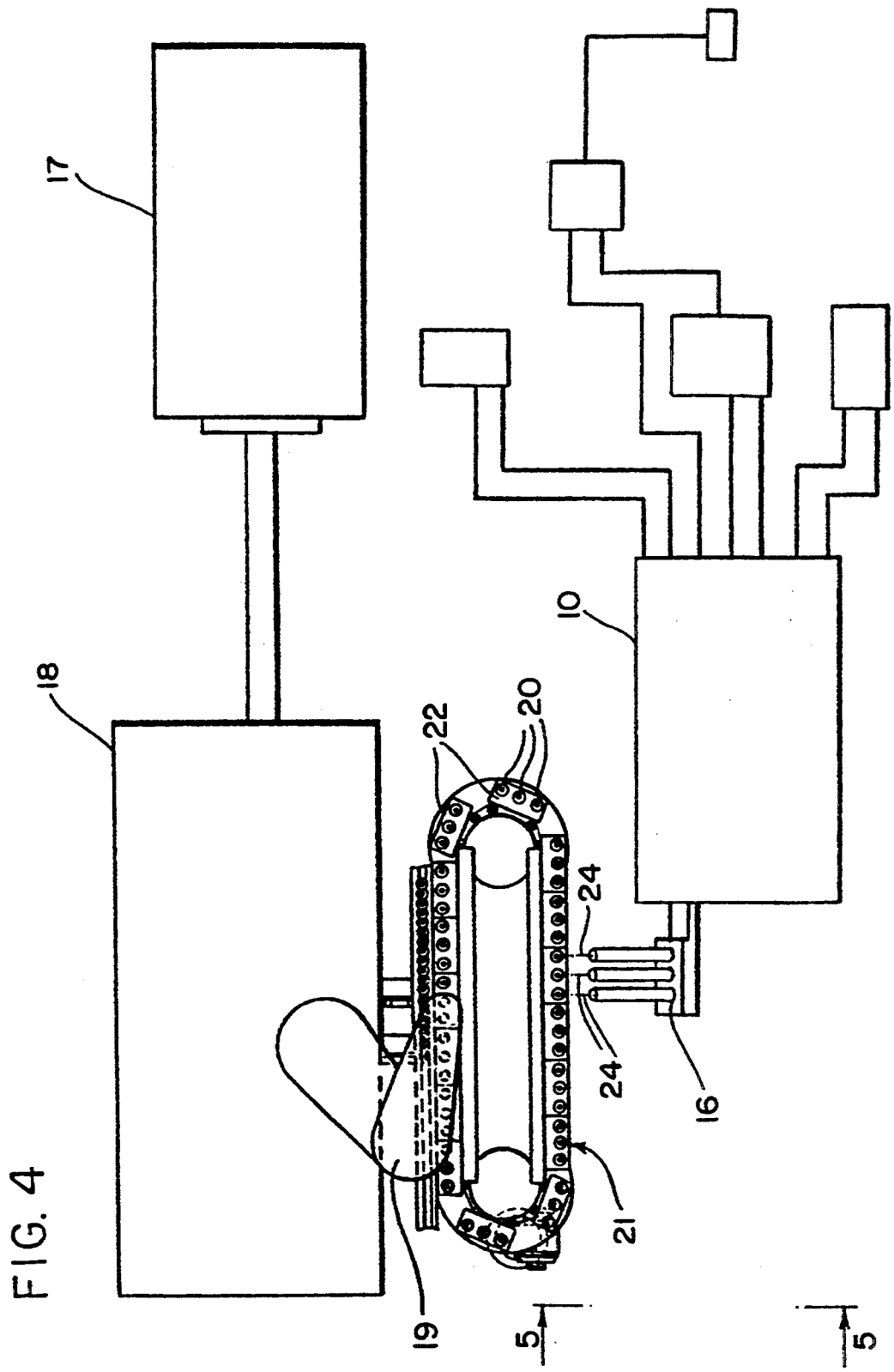
FIG. 4 is a schematic representation of the handling process of the present invention.

Referring to FIG. 4, there are shown the schematic set up of an assembly and manufacturing apparatus for catheters of the invention. An initial fabrication set up and supply indicated schematically by areas 17 and 18 is used to make conventional catheters. For example, a polyurethane catheter attached to a polymer hub, which is placed on a sharpened cannula for insertion. The initial fabrication of the catheter tube and hub may be the same as that currently used by those of ordinary skill in the art. The catheter is formed either with the initial 3° taper indicated previously, or left as a straight tube. The catheter and needle assembly is then removed from the fabrication machine by arm 19 and placed on a carrier 20 on positioner 21. Positioner 21 has a series of carriages 22, each having positions for three catheter and cannula subassemblies. The carriages are rotated about the positioner 21 as will be described below and brought into a set position. The catheter and cannula subassembly is positioned where it will intercept one of the split beams 24 and is rotated at a given speed. For example, at approximately three rotations per second. However, the rotation speed may be at six rotations or higher. The catheter and cannula subassembly is exposed to the laser for approximately 2 seconds. This time is determined by the pulse repetition rate and the energy of the laser beam. The number of pulses being selected such that the speed of forming the product is optimized while using an amount of energy that does not overly heat the product or cause melting or other destruction of the tip.

Figure 5:
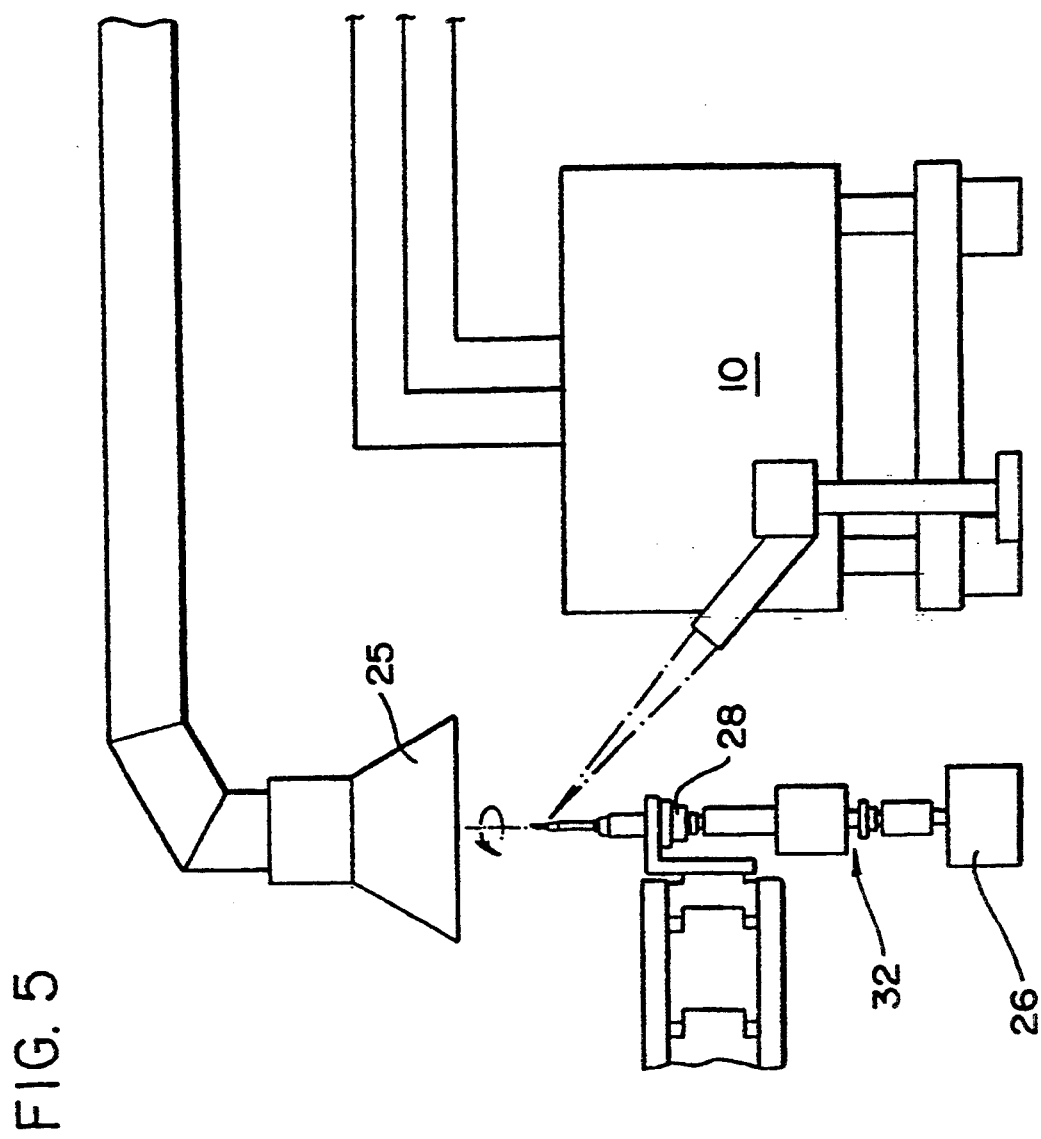
FIG. 5 is a side elevation view of the apparatus of the present invention.
Figure 6:
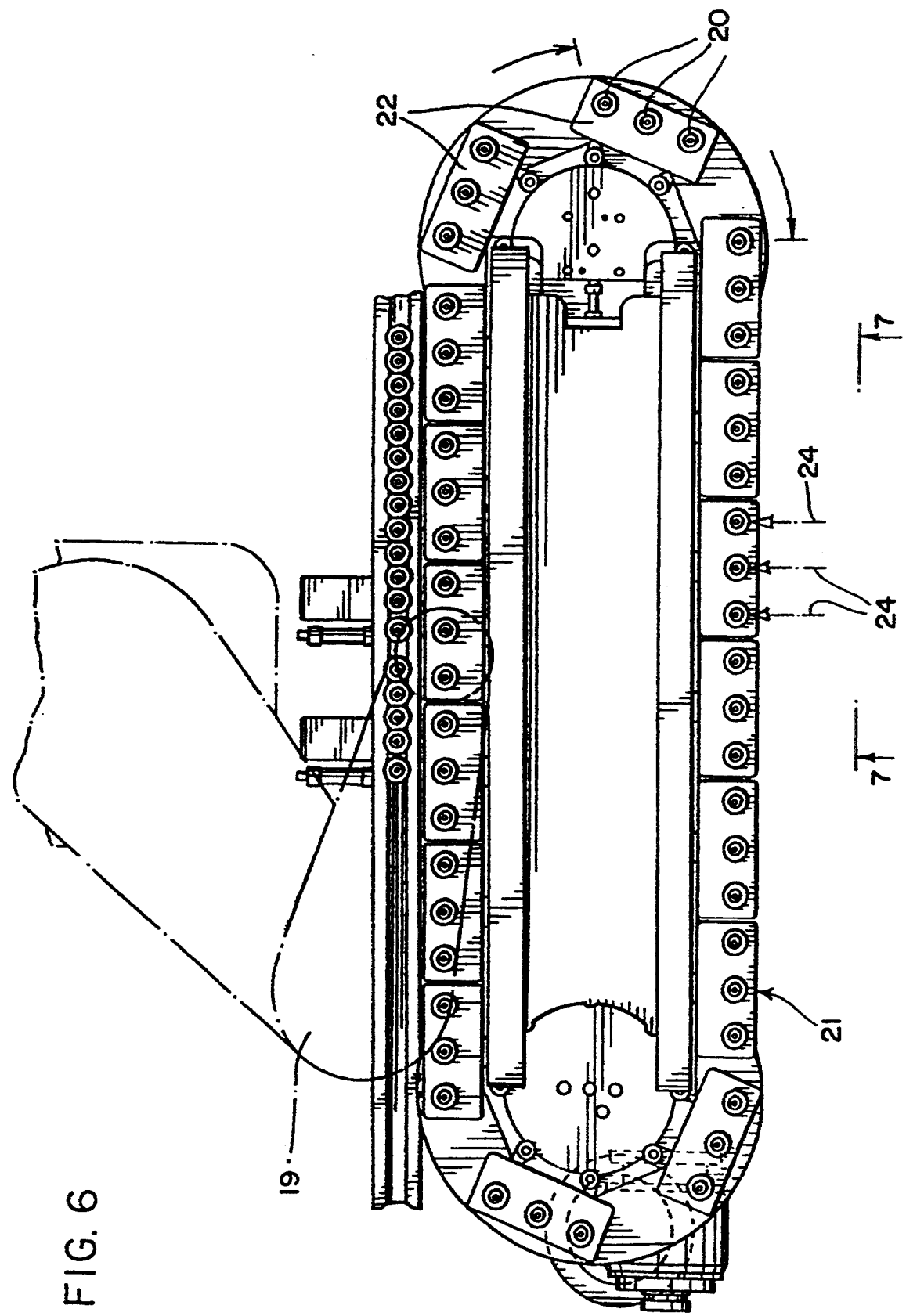
FIG. 6 is a top plan view of the positioning and handling portion of the apparatus.

During the impingement of the laser beam on the product, the catheter material is ablated in a conical shape due to the rotation of the catheter and cannula subassembly, and positioning such subassembly at a 45°±2° angle to the laser beam direction, as shown in FIG. 5. This ablation causes a release of polymer molecules and by-products, which are removed from the manufacturing area through hood 25. If an exceptionally long catheter tube is used, it may be necessary to provide a vacuum source at the tip of the cannula to pull any residual catheter portion above the zone of the laser impingement off the catheter and remove it from the cannula.

Figure 7:
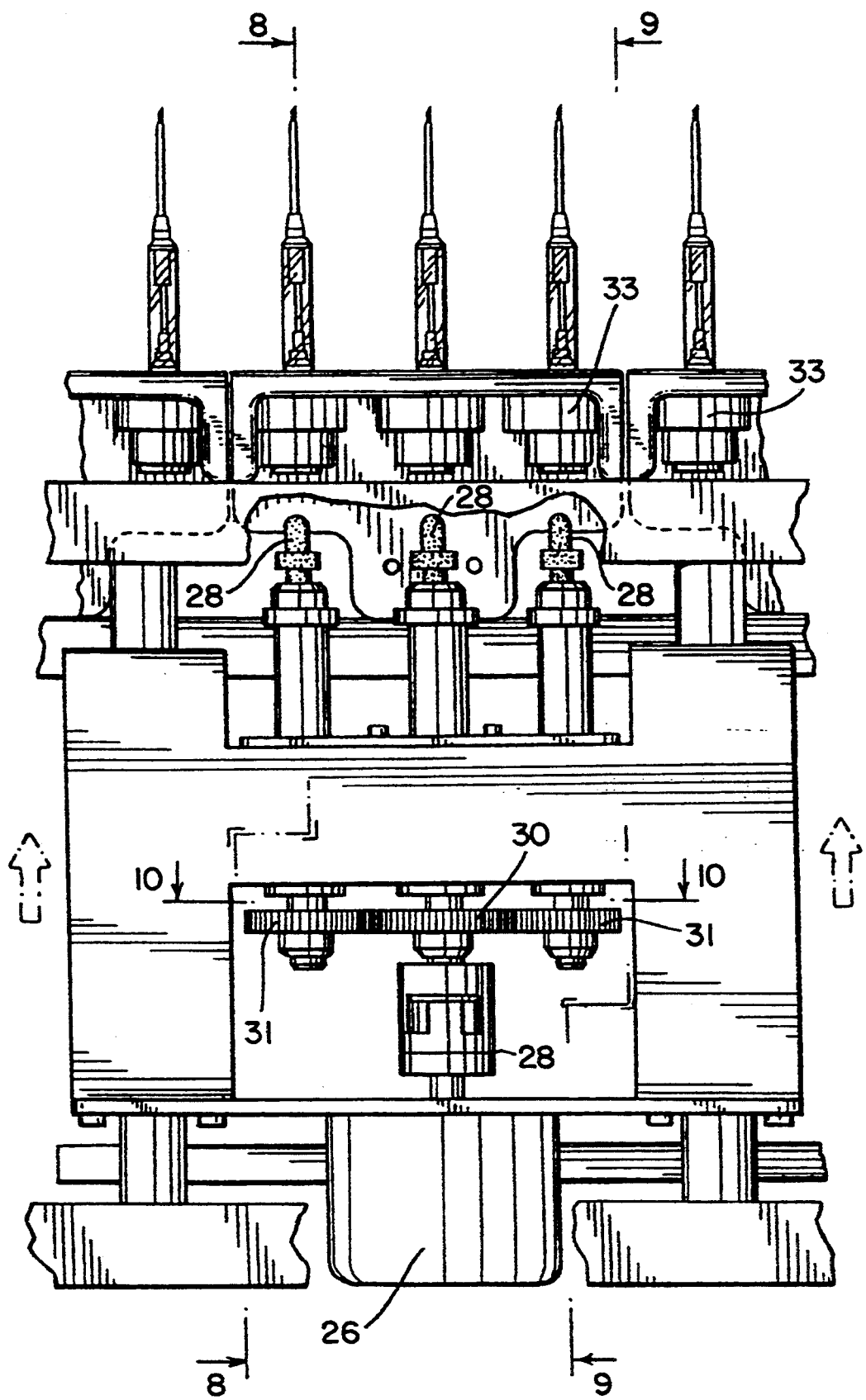
FIG. 7 is a partially broken away view of the spinning portion of the apparatus.
Figure 8:
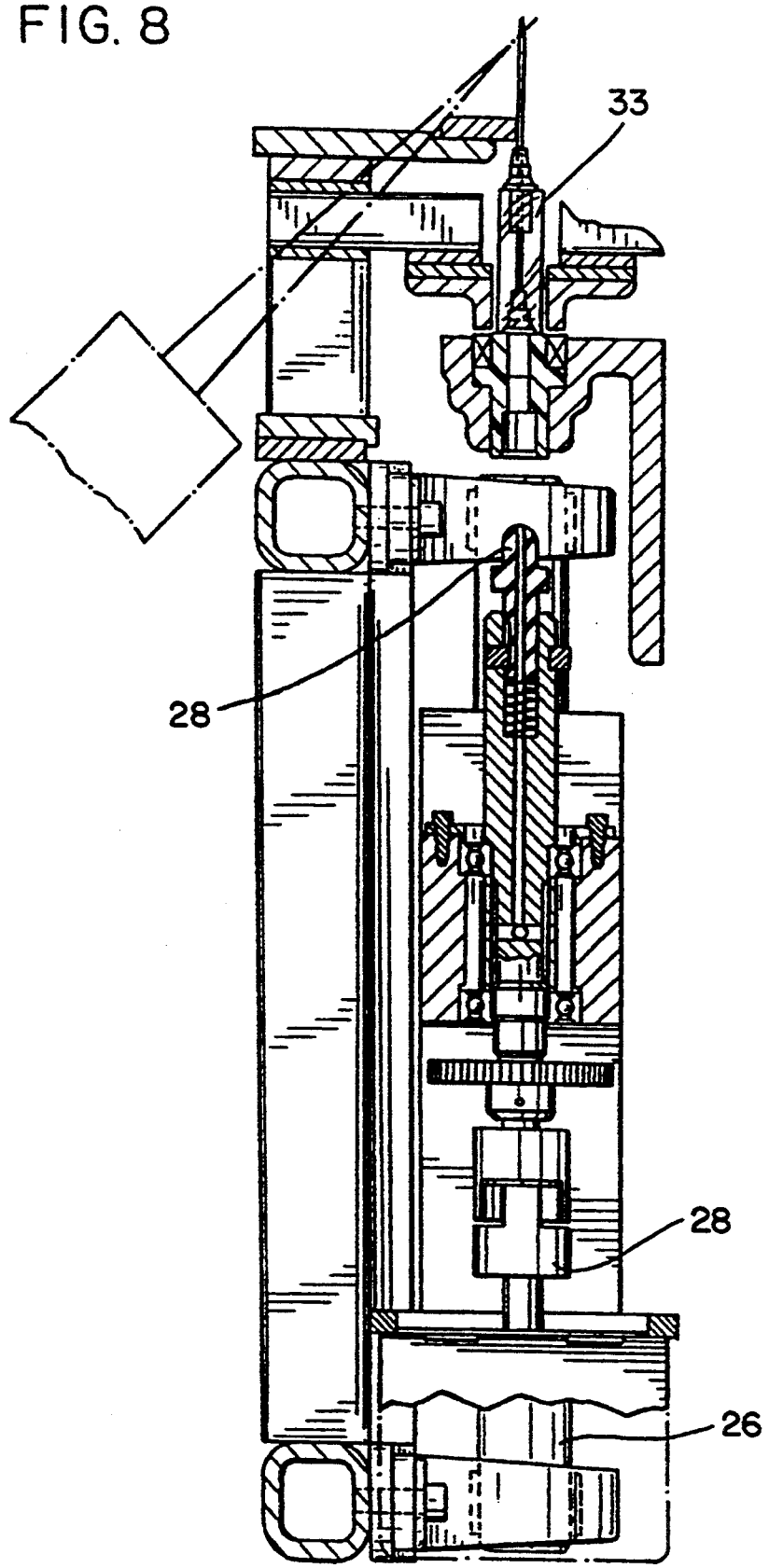
FIG. 8 is a cross-sectional view of FIG. 7 taken along lines 8—8.
Figure 10:
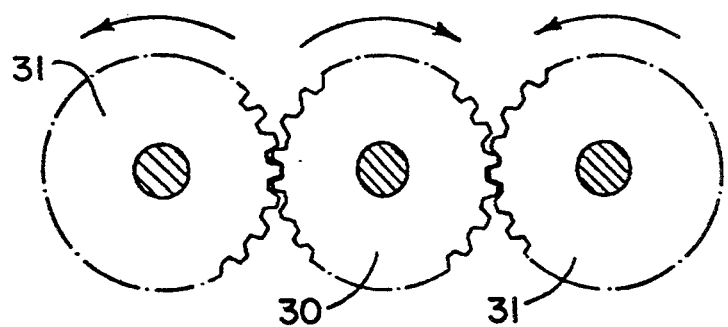
FIG. 10 is a view taken along lines 10—10 of FIG. 7.

The catheter and cannula subassembly is rotated through the use of a motor and transmission subassembly, which is shown schematically in FIG. 5. The motor 26 rotates the assemble through a transmission 27, and a clutch 28. The clutch 28 and motor assembly are moved vertically to engage the bottom of the carrier to rotate the catheter and cannula subassembly. Although the speed of rotation is controlled, the point at which the clutch engages and disengages need not be controlled with finite accuracy. The catheter and cannula subassembly is rotated and the timing of the process is controlled by the initiation and termination of the laser impingement on the product. Therefore, the product is started along its rotational motion and then the laser is turned on to form the beveled end. After the laser has been turned off, the clutch 28 motor 26 and transmission 27 are dropped out of engagement with the carriage and the carriage is repositioned. As can be seen more clearly in FIG. 7, the transmission 27 provides a group of three clutches 28. The transmission 27, through the use of a gear system indicated in FIG. 10, transmits power to driven gears 31 through drive gear 30. Driven gears 31 are driven at the same speed as drive gear 30, thus maintaining consistency in the manufacturing operation.

Figure 9:
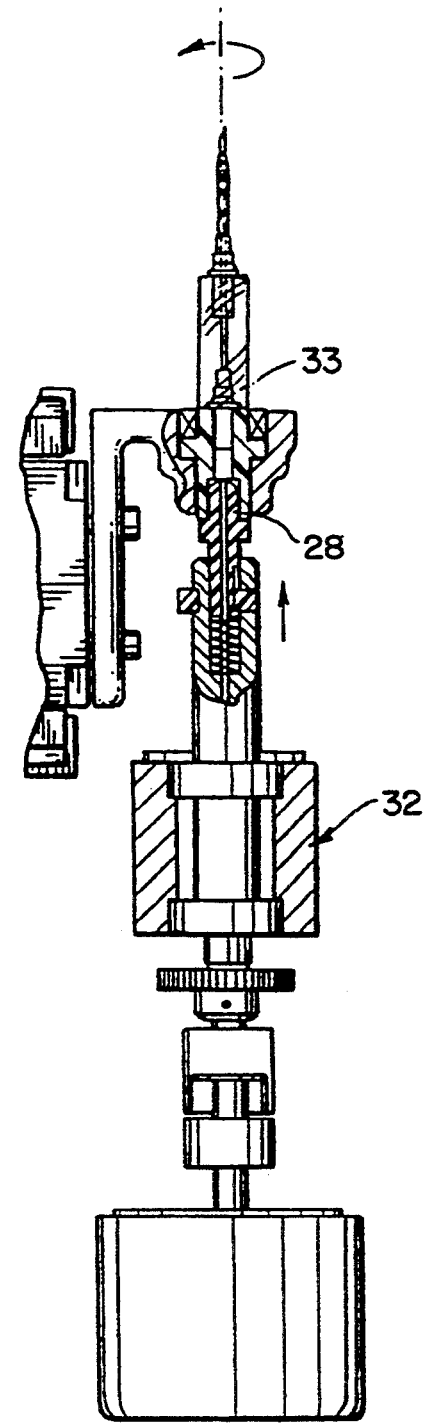
FIG. 9 is a cross-sectional view of FIG. 7 taken along lines 9—9.

The entire drive assembly 32, which consists of the transmissions, motor and clutch mechanisms is raised and lowered into engagement with the holders 33 in the carriage 20. Each holder 33 has provided thereon a catheter and cannula subassembly such that the raising of the drive assembly 32 engages the clutch 28 of each respective holder 33 and thereby drives the rotation of catheter and cannula subassembly (FIG. 9). After formation of the bevel, the carriage is rotated out of position back to the start of the carrier 20 and arm 19 removes the product from the carriage and returns it to the assembly process for final assembly of the catheter. This assembly may merely require the addition of a shield to the catheter product or may require further fabrication steps to make a desired final fabrication assembly.

By adjustment of the power and focus of the laser beam 11, a zone 7 may be formed on the cannula surface. This zone is believed to be a surface finishing of the stainless steel cannula, which is the preferred cannula used in the process. This cannula is a 304 stainless steel and it is believed that the laser either removes the natural oxidation from the surface of the cannula and subsequently produces a zone with a higher concentration of chromium than is found in the normal surface of the cannula. This zone can be manipulated to be of a significant size or virtually non-existent. It has been found to preferably create a zone of approximately 1 mm inches wide, which provides a visual indication of the end of an optically clear catheter material.

Furthermore, it has been found that the catheter material may be lightly sealed to the outer surface of the cannula, thus reducing or preventing the leakage of blood between the catheter and cannula during the insertion process. This sealing has been provided with such limited strength that it does not significantly reduce the performance of the product in the removal of the cannula from the catheter.

The invention has been described in its preferred embodiment. It can easily been seen by one of ordinary skill in the art that many modifications may be made to the preferred embodiment without leaving the scope of the invention.

We claim:

1. A process for beveling a tip of a catheter having a tubular sheath and longitudinal axis comprising:
   a) providing a source of coherent light with sufficient power to ablate the catheter material;
   b) positioning said catheter in a path of said coherent light with said longitudinal axis at a predetermined angle to said path; and
   c) rotating said catheter while impinging said coherent light on said catheter along a predetermined path to ablate catheter material at a predetermined tip location to form a frusto conical tip surface.

2. The process according to claim 1 wherein the catheter is positioned upon a cannula prior to impinging coherent light on the catheter.

3. The process according to claim 2 wherein the coherent light impinges on the cannula surface and changes the catheter surface in the area of impingement to differ from the remaining cannula surface.

4. The process according to claim 1 wherein the source of coherent light has a cross sectional shape and power which ablates said catheter material in a concave shape.

5. The process according to claim 1 wherein the cross sectional shape end power of the coherent light impinging on the catheter is shaped to create a convex tip shape.

6. The process according to claim 1 wherein said predetermined path is approximately 45° to a longitudinal axis of said catheter.

7. The process according to claim 1 wherein said coherent light is shaped by passing said beam through a slit mask.

8. A process for beveling a tip of a catheter having a tubular sheath comprising:
   a) providing a pre-molded tubular sheath having a predetermined bevel on the outer surface thereof;
   b) positioning said catheter at a predetermined position;
   c) impinging an incident beam of coherent light upon such catheter at a predetermined position an angle while rotating said catheter to trim said catheter at said predetermined position.

9. A process according to claim 9 wherein said catheter is provided with a needle therein and said incident beam of light is directed and focused to change the surface of said needle during said trimming process.

10. The process according to claim 9 wherein the surface effect is to increase reflectivity of the surface of said needle at a position adjacent the end of said catheter.

11. The process according to claim 10 wherein said needle is stainless steel.

12. A process for simultaneously trimming and providing surface effect to a catheter and needle respectively comprising:
   a) positioning a catheter on a needle to provide a catheter needle subassembly;
   b) positioning said catheter and needle subassembly at a predetermined position;
   c) rotating said catheter and needle subassembly at said predetermined position while impinging thereon a beam of coherent light of sufficient energy to ablate the catheter substance;
   d) providing said beam of coherent light for sufficient time and at a predetermined angle to ablate the circumference of the catheter forming a bevel tip and to impinge upon the surface of the needle with sufficient energy to visually modify the surface thereof.

13. The process according to claim 12 wherein said surface effect modifies the surface of said needle by removing an oxidized layer from the surface of said needle.

14. The process according to claim 12 wherein said needle is stainless steel.

15. The process according to claim 14 wherein said needle is 304 stainless steel.

16. The process according to claim 12 wherein said surface effect modifies the surface of said needle by increasing the concentration of chromium at the surface of a stainless steel needle.

* * * * *